United States Patent [19]
Markowitz et al.

[11] Patent Number: 5,514,163
[45] Date of Patent: May 7, 1996

[54] DUAL CHAMBER PACING SYSTEM AND METHOD WITH OPTIMIZED ADJUSTMENT OF THE AV ESCAPE INTERVAL FOR TREATING CARDIOMYOPATHY

[75] Inventors: H. Toby Markowitz, Roseville; Tom D. Bennett, Shoreview, both of Minn.

[73] Assignee: Medtronic, Inc., Minneapolis, Minn.

[21] Appl. No.: 391,947

[22] Filed: Feb. 21, 1995

[51] Int. Cl.$^6$ ..................................................... A61N 1/362
[52] U.S. Cl. ................................................................ 607/9
[58] Field of Search ................................ 607/9, 25, 26, 607/27, 28, 17, 18

[56] References Cited

U.S. PATENT DOCUMENTS

| | | |
|---|---|---|
| 4,428,378 | 1/1984 | Anderson . |
| 5,052,388 | 10/1991 | Sivula . |
| 5,247,929 | 9/1993 | Stoop et al. ............................. 607/14 |
| 5,334,220 | 8/1994 | Sholder . |
| 5,340,361 | 8/1994 | Sholder . |

OTHER PUBLICATIONS

McDonald, Kenneth et al., "Permanent Pacing as Treatment for Hypertrophic Cardiomyopathy", The American Journal of Cardiology, vol. 68, Jul. 1991, pp. 108–110.
Jeanrenaud, Xavier et al., "Effects of Dual–Chamber Pacing in Hypertrophic Obstructive Cardiomyopathy," The Lancet, vol. 339, May 1992, pp. 1318–1323.
McAreavey, Dorothea et al., "Altered Cardiac Hemodynamic and Electrical State in Normal Sinus Rhythm After Chronic Dual–Chamber Pacing for Relief of Left Ventricular Outflow Obstruction in Hypertrophic Cardiomyopathy", American Journal of Cardiology, vol. 7, Sep. 1992, pp. 651–656.
Seidelin, P. H., "Effects of Dual–Chamber Pacing in Hypertrophic Cardiomyopathy without Obstruction", The Lancet, vol. 340, Aug., 1992, pp. 369–370.
Boute, W., et al., "Morphology of Endocardial T–Waves of Fusion Beats", Pace, vol. 11, Nov. 1988, Part II, pp. 1693–1697.
Parsonnet, et al., "The Development of an Intracadiac Dipolar Catheter Electrode for the Treatment of Complete Heart Block", Surgical Forum.
Fananapazir, et al., "Impact of Dual Chamber Permanent Pacing in Patients with Obstructive Hypertrophic Cardiomyopathy with Symptoms Refractory to Verapamil and β–Adrenergic Blocker Therapy", Circulation, vol. 8, No. 6, Jun., 1992, pp. 2149–2161.

Primary Examiner—William E. Kamm
Assistant Examiner—Scott M. Getzow
Attorney, Agent, or Firm—Harold R. Patton; Michael B. Atlass

[57] ABSTRACT

A dual chamber pacemaker system and method are provided for HOCM and like pacing therapy, with the feature of searching or scanning values of AV escape interval to define an optimized value at about the longest AV escape interval value consistent with full capture in response to a delivered ventricular pace pulse. In a preferred embodiment of the invention, the system and method sense and process FFRS signals derived from the atrial lead and otherwise, and obtain therefrom a characteristic which is evaluated for a determination of optimized AV escape interval. In one specific embodiment, the time durations between delivered ventricular pacing pulses and resulting FFRS signals are analyzed as a function of AV escape interval, and the optimized AV escape interval is chosen at about the longest AV escape interval corresponding to the longest such time duration, i.e., at about the knee of the FFRS time duration vs. AV escape interval curve. In another embodiment, the FFRS characteristic utilized is duration, and the system determines the longest AV escape interval corresponding to the highest duration value. The system and method can be utilized either with an external programmer or can be adapted to operate automatically in an implanted pacemaker.

34 Claims, 7 Drawing Sheets

DUAL CHAMBER PACING SYSTEM AND METHOD WITH OPTIMIZED ADJUSTMENT OF THE AV ESCAPE INTERVAL FOR TREATING CARDIOMYOPATHY

BACKGROUND OF THE INVENTION

This invention relates to cardiac pacing systems and methods generally and, in particular, to dual chamber cardiac pacing systems and methods for delivering ventricular pacing pulses synchronized to atrial signals so as to benefit patients with cardiomyopathy and forms of congestive heart failure (CHF), and in particular Hypertrophic Obstructive Cardiomyopathy.

Hypertrophic Obstructive Cardiomyopathy (HOCM) is characterized by a narrowed left ventricular outflow tract (LVOT), which causes a significant increase in the left ventricular end systolic pressure. The narrowed LVOT is caused by an increased thickness of the interventricular septum which obstructs blood flow during systole, the time of cardiac ejection.

Symptomatic improvement of patients with HOCM can be obtained in some cases with the use of standard pharmacotherapy. However, drugs in use for this therapy have disadvantages which have been cited in the literature. Likewise, surgical intervention, e.g., septal myectomy or mitral valve replacement, is another optional treatment. However, such surgical treatments carry a significant operative mortality and have not been shown to alter the natural history of the disease. See, "Permanent Pacing As Treatment For Hypertrophic Cardiomyopathy," by Kenneth M. McDonald et al., *American Journal of Cardiology*, Vol. 68, pp. 108–110, July 1991.

The value of dual chamber cardiac pacing and treatment of patients suffering from HOCM has been recognized in the literature. Modern multiple-mode, dual-chamber cardiac pacemakers are designed to maintain AV synchrony for damaged or diseased hearts that are unable to do so on their own. For example, a DDD pacemaker has electrical connections to both the atrium and the ventricle, senses electrical signals in both chambers of the patient's heart, and delivers atrial pacing stimuli in the absence of signals indicative of natural atrial activation, and ventricular pacing stimuli in the absence of signals indicative of natural ventricular activation. Such a dual chamber pacemaker maintains the AV synchrony of the heart by delivering ventricular pace pulses at a controlled AV interval following each atrial event.

Studies have indicated that patients suffering from HOCM may benefit from a specific mode of dual chamber pacing wherein a ventricular pacing pulse is delivered in timed synchrony with the sensed or paced atrial depolarization. Pacing the right ventricular apex before spontaneous atrioventricular conduction activates the ventricles is understood to alter the ventricular septal activation pattern. Since the right ventricle is caused to contract first, it pulls the septum toward the right ventricle thereby reducing the LVOT obstruction.

The literature uniformly acknowledges the potential advantages of synchronized A–V pacing for HOCM patients, stressing the importance of achieving ventricular capture. Causing "complete ventricular capture" is important to obtain the above-described septal movement, while selecting the longest AV delay that results in complete ventricular capture is important in order to maximize the atrial contribution to ventricular filling. See U.S. application Ser. No. 08/214,933, filed Mar. 17, 1994, Method and Apparatus For Dual Chamber Cardiac Pacing, assigned to Medtronic, Inc., and the literature articles referenced therein. The delivered pacing pulse should provide "pre-excitation," i.e., depolarization of the ventricular apex before the septum. This altered pattern of septal contraction, as well as optimal left ventricular filling, is generally recognized as being important to this mode of pacemaker treatment. Further, it appears to be established that such synchronized AV pacing provides HOCM patients a long-term benefit, i.e., the benefit remains even after cessation of pacing, since such AV pacing causes a reduction in the obstruction of the LVOT which persists in sinus rhythm after cessation of pacing. However, the duration of the benefit is not certain.

The literature suggests that the AV escape interval should be set at the longest duration that maintains ventricular capture at different exercise levels. See the above-cited McDonald article. It has been suggested that the AV escape interval which allows for maximal pre-excitation of the ventricle by the pacing pulse can be selected by determining the AV escape interval that produces the widest paced QRS complex duration, as seen on a surface electrocardiogram. See "Impact of Dual Chamber Permanent Pacing in Patients With Obstructive Hypertrophic Cardiomyopathy With Symptoms Refractory to Verapamil and β-Adrenergic Blocker Therapy," by Fananapazir et al., *Circulation*, Vol. 8, No. 6, June 1992, pp. 2149–2161.

In the referenced U.S. application assigned to Medtronic, Inc., the pacemaker periodically checks to determine a value of intrinsic AV conduction time (AVC) and subtracts therefrom a ventricular sense offset interval (VSO) to get the AV escape interval. After a waveform of the ventricular depolarization resulting from complete capture is noted and recorded for comparison, the AV escape interval is set to a lengthened value, resulting in one or more ventricular sense events. The value of AVC is determined as the time difference between the atrial event and the sensed R-wave. Following this, the pacemaker AV escape interval is reduced further until the pacemaker finds an R wave with a waveform that indicates good capture. The difference between AVC and the capture value of A–V is VSO, and the pacemaker thereafter sets AV= AVC–VSO.

The prior art techniques for AV synchronous pacing of HOCM patients recognize the necessity to periodically evaluate the AV delay, or AV escape interval. The patient's spontaneous atrio-ventricular conduction time generally will change with heart rate, i.e., from rest to exercise. Moreover, simultaneous drug treatment such as beta blockers may also modify AV conduction time and require renewed evaluation of the AV delay. The importance of periodically making an accurate determination of the optimized AV interval thus takes on significance. If the AV delay is adjusted to a value which is too short, in order to ensure complete ventricular capture, the atrial contribution to ventricular filling may be compromised. However, if the AV escape interval is adjusted to too great a value, ventricular capture is compromised, and there may be episodes of no ventricular pacing or the ventricular pace may not contribute the best possible reduction of the LVOT obstruction. Accordingly, it is important in this therapy to be able to continuously or periodically adjust the AV escape interval to optimize it for HOCM therapy.

SUMMARY OF THE INVENTION

This invention provides an apparatus and method for adjustment of the AV delay for dual chamber pacing therapy in patients with HOCM. The apparatus and method are based upon an improved method for determining the optimum AV escape interval, including both the means of detecting data from which the optimum interval can be derived, and the operating algorithm for finding an optimized operating value of AV delay. The terms AV delay and AV escape interval ($AV_{esc}$) are used interchangeably.

In a first preferred embodiment, the pacemaker and method of this invention locate the far field R-wave sense (FFRS) and utilize data from the FFRS signals for determining the optimum AV interval. As is known, the FFRS is a representation, or measure of the QRS, but sensed in the atrium. More specifically, one embodiment is based upon our observation that patients with HOCM and like conditions are likely to produce an FFRS which is late relative to the delivered ventricular pacing pulse. Accordingly, a method of the invention is to adjust the AV interval through a series of respective values, and measure the time between each ventricular pacing pulse and the following FFRS or QRS, i.e., the VP-FFRS or VP-QRS time. The pacemaker determines the $AV_{esc}$ corresponding to the longest VP-FFRS time, which longest time corresponds to the latest septal activation and accordingly represents an optimized value of AV escape interval. The $AV_{esc}$ is then reset in accord with the determined optional AV value. More specifically, the pacemaker incorporates an algorithm for determining the knee of the VP-FFRS or VP-QRS curve, and sets the AV interval to a value just slightly less than the knee. Likewise, the FFRS duration, or QRS duration or "width" reaches a maximum value as the AV interval is shortened to about the longest value consistent with good capture. A second method thus involves similarly adjusting the AV escape interval, e.g., scanning from a relatively high AV value resulting in natural ventricular depolarizations, toward shorter values which result in capture and evoked R-waves, and measuring corresponding values of FFRS or QRS duration. After the duration data is obtained from the scan, an algorithm analyzes the data and determines the $AV_{esc}$ value corresponding to the breakpoint where QRS or FFRS duration reaches a high value plateau.

The invention can be practiced either by adjusting AV escape interval when the patient presents for programming, or when the patient is ambulatory. In the case of a patient whose pacemaker is in communication with a programmer, the algorithm-driving data may be obtained from the ECG as recorded from skin electrodes which are connected to the programmer; from sub-Q electrodes as used in a syncope monitor; or from the far field electrogram as recorded from the atrial channel of the pacemaker and communicated to the programmer. The programmer collects and displays the appropriate data so that the physician can inspect it and pick the desired AV setting or, alternatively, the pacemaker system can automatically select the optimum setting and present it to the physician as a recommended value. In the case of an implanted pacemaker, the pacemaker can continuously or periodically, e.g., once a day or more frequently, determine a new adjusted AV escape interval and override the previously programmed value.

BRIEF DESCRIPTION THE DRAWINGS

Figure 6A:
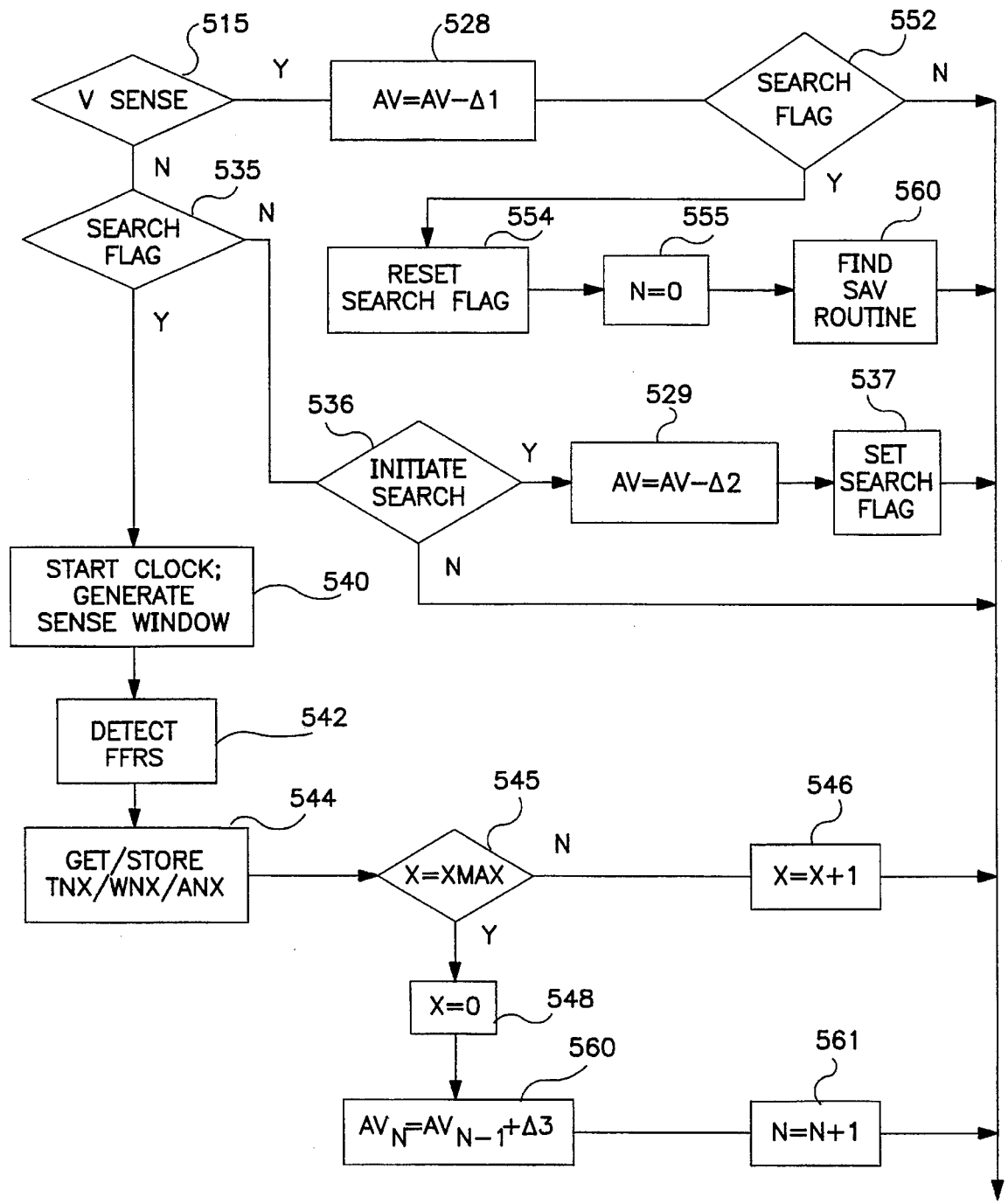
Figure 6B:
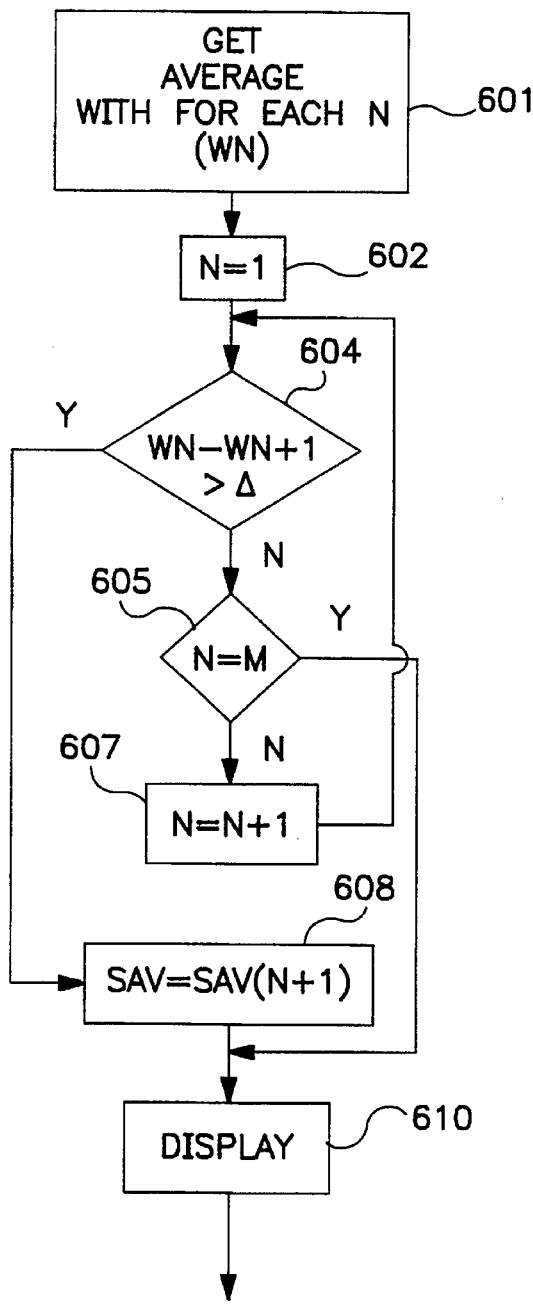
Figure 6C:
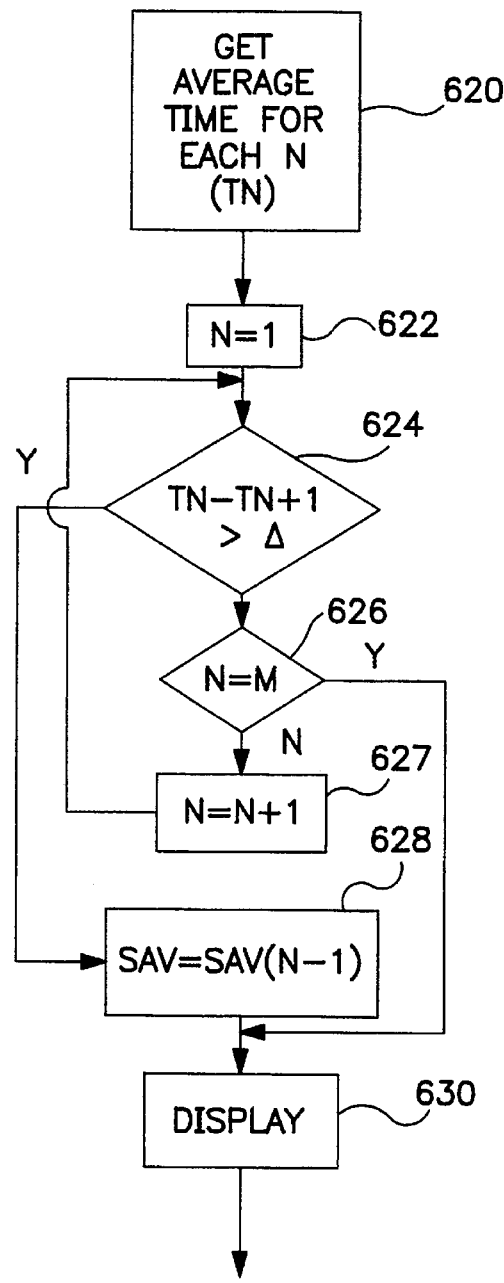

FIG. 6A is a flow diagram illustrating steps taken by the pacemaker system of this invention in acquiring data for a determination of AV interval adjustment; FIG. 6B is a flow diagram of a routine for determining optimized AV escape interval from data representative of FFRS or QRS duration; FIG. 6C is a flow diagram of a routine for determining optimized AV escape interval from data representative of the time interval between ventricular pace pulses and evoked QRS or FFRS signals.

DETAILED DESCRIPTION OF THE PREFERRED EMBODIMENTS

Figure 1:
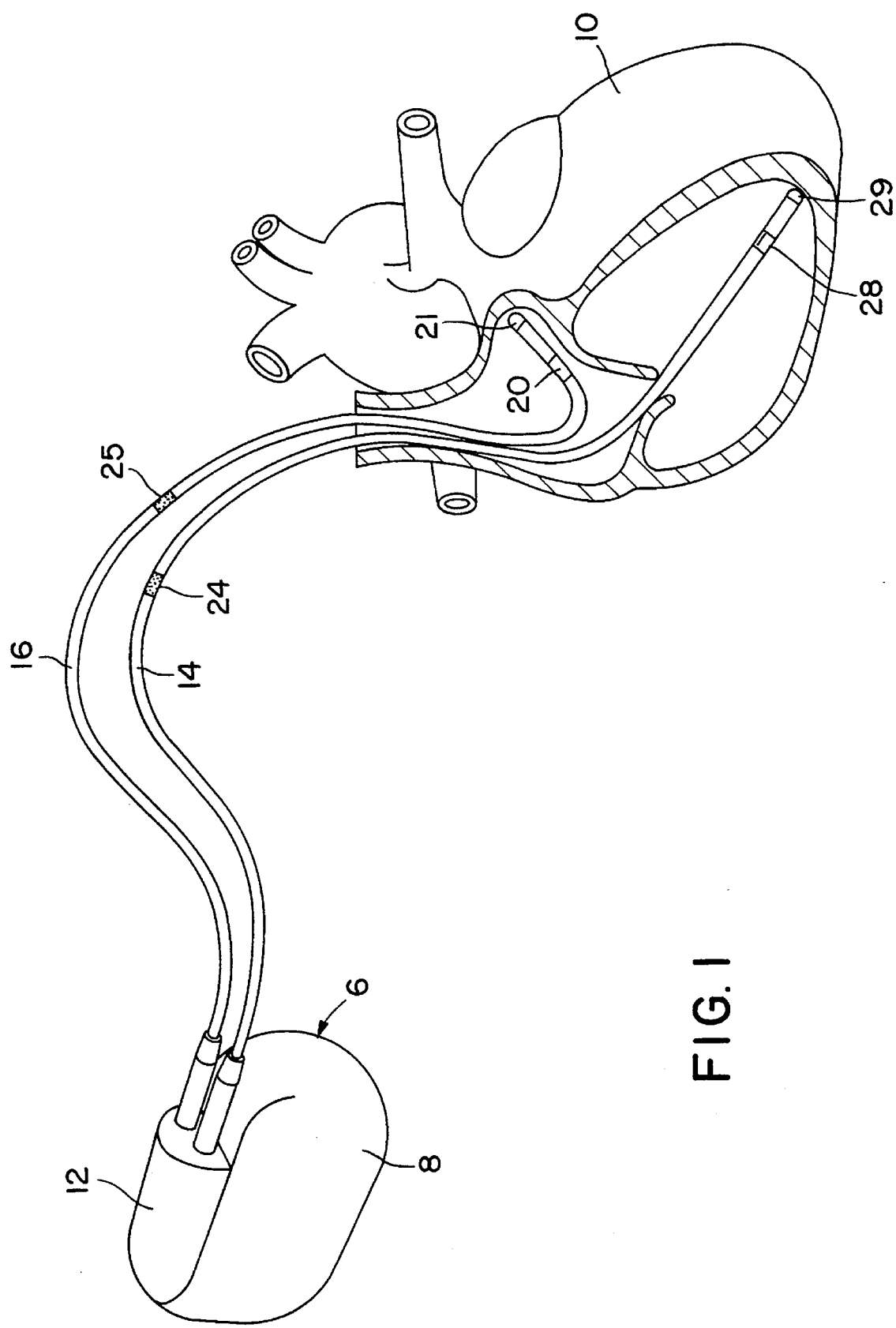
FIG. 1 is a perspective representation of the pacemaker system of this invention showing an implantable pacemaker connected to a patient's heart.

FIG. 1 illustrates the external configuration of a dual chamber pacemaker 6, which is provided with a hermetically sealed enclosure 8, typically fabricated of biocompatible metal such as titanium. Mounted to the top of the enclosure 8 is a connector block assembly 12, which receives electrical connectors located on the proximal ends of leads 14 and 16. Lead 16 is an atrial pacing lead, carrying two electrodes 20 and 21. Electrodes 20 and 21 are used both to sense atrial depolarizations and to deliver atrial pacing pulses. Atrial pacing pulses may be delivered between electrode 20 and electrode 21 or between electrode 21 and the housing 8 of the pacemaker 6. Sensing of atrial depolarizations may occur between electrode 20 and electrode 21 or between either of electrode 20 and 21 and the housing 8 of the pacemaker 6. Also, alternately, FFRS signals may be detected by electrodes placed at other positions, e.g., at locations 24, 25.

Similarly, lead 14 represents a ventricular bipolar pacing lead, carrying two electrodes 28 and 29. As discussed above in conjunction with atrial lead 16, electrodes 28 and 29 are used to sense and pace the ventricle. Ventricular pacing may be accomplished between electrodes 29 and 28 or between electrode 29 and the conductive housing 8 of pacemaker 6. Sensing of ventricular signals, including depolarizations (QRS-waves) and repolarizations (T-waves) may be accomplished between electrodes 29 and 28 or between either of electrodes 29 and 28 and the housing 8 of the pacemaker 6.

As discussed in the present application, the preferred embodiments of the pacemaker 6 operate in a DDD or DDDR pacing mode, wherein pacing pulses are delivered to both atrium and ventricle and wherein atrial and ventricular depolarizations are both effective to inhibit delivery of the next scheduled pacing pulse in the chamber in which they are detected. While the present invention is believed optimally practiced in a pacemaker operating in DDD pacing mode, in some patients there may also be a benefit to operating the device in VDD or DVI mode, which provides ventricular pacing pulses synchronized only to sensed atrial depolarizations or only delivered to atrial pacing pulses, respectively, depending upon the specific underlying heart condition of the patient. However, DDD mode is expected to be the mode most widely used to practice the present invention.

Figure 2:
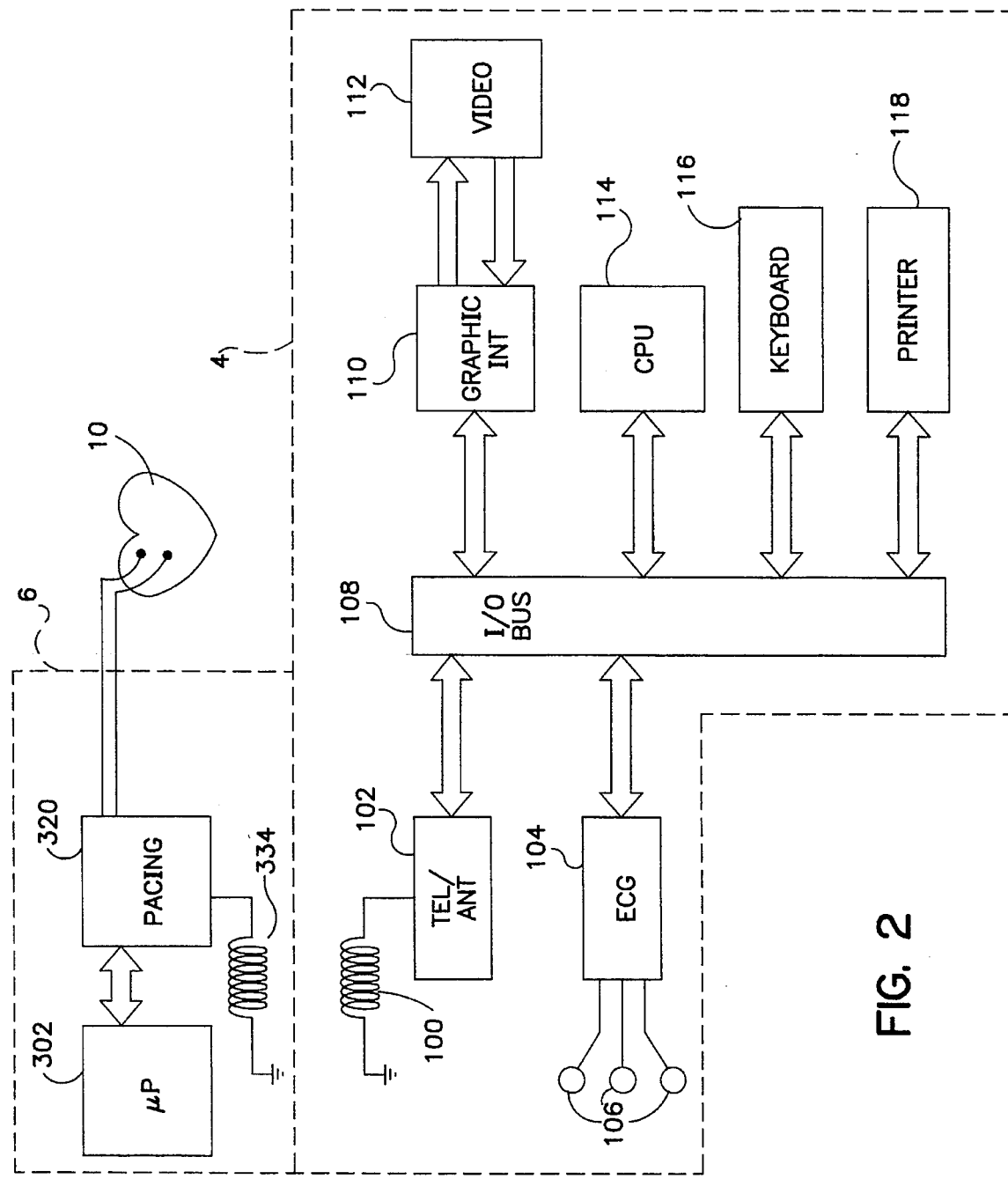
FIG. 2 is a block diagram of the pacemaker system of this invention, showing a pacemaker inter-connected with an external programmer and with ECG leads.

FIG. 2 illustrates the pacemaker 6 in block diagram form, coupled to a human heart 10, in conjunction with an external programmer/display apparatus corresponding to those typically employed to program modern, multi-programmable implantable pacemakers. Within the housing of the pacemaker are located the pacing circuitry 320, which includes circuitry performing all of the basic timing, stimulation and sensing functions of a cardiac pacemaker and a microprocessor circuit 302, which controls the timing intervals provided by the pacing circuitry 320. Pacing circuitry 320 also includes a bidirectional telemetry circuit coupled to an antenna 334, allowing transmission of information from external programmer 4 into the pacemaker 6 to modify its parameters and allowing transmission of information from the pacemaker 6 to the external programmer 4, again generally corresponding to telemetry and programming systems presently existing in commercially marketed multi-programmable in implantable pacemakers.

The programmer 4 also includes a corresponding antenna 100 coupled to a telemetry/antenna driver circuit 102 which serves to demodulate telemetry signals received from antenna 334 of the pacemaker, and to apply them in parallel or serial digital format to input output (I/O) unit 108, where they in turn may be applied to a video monitor 112 via graphic interface 110, and/or provided to central processing unit 114 and/or printer 118. Microprocessor 114 controls the operation of the programmer/display apparatus, and is responsive to physician entered commands via keyboard 116, for controlling programming signals sent to the pacemaker, as well as for controlling operation of the video display 112 and printer 118. Also illustrated is an ECG interface 104, coupled to three ECG electrodes 106 which can be placed upon the patient's body. ECG interface 104 provides sensed electrograms to input/output device 108, where they in turn may be provided to the video display 112, the central processing unit 114 or the printer 118. The ECG capability is used for treatment according to the method of this invention for a patient who is available for initial or subsequent programming.

Figure 3:
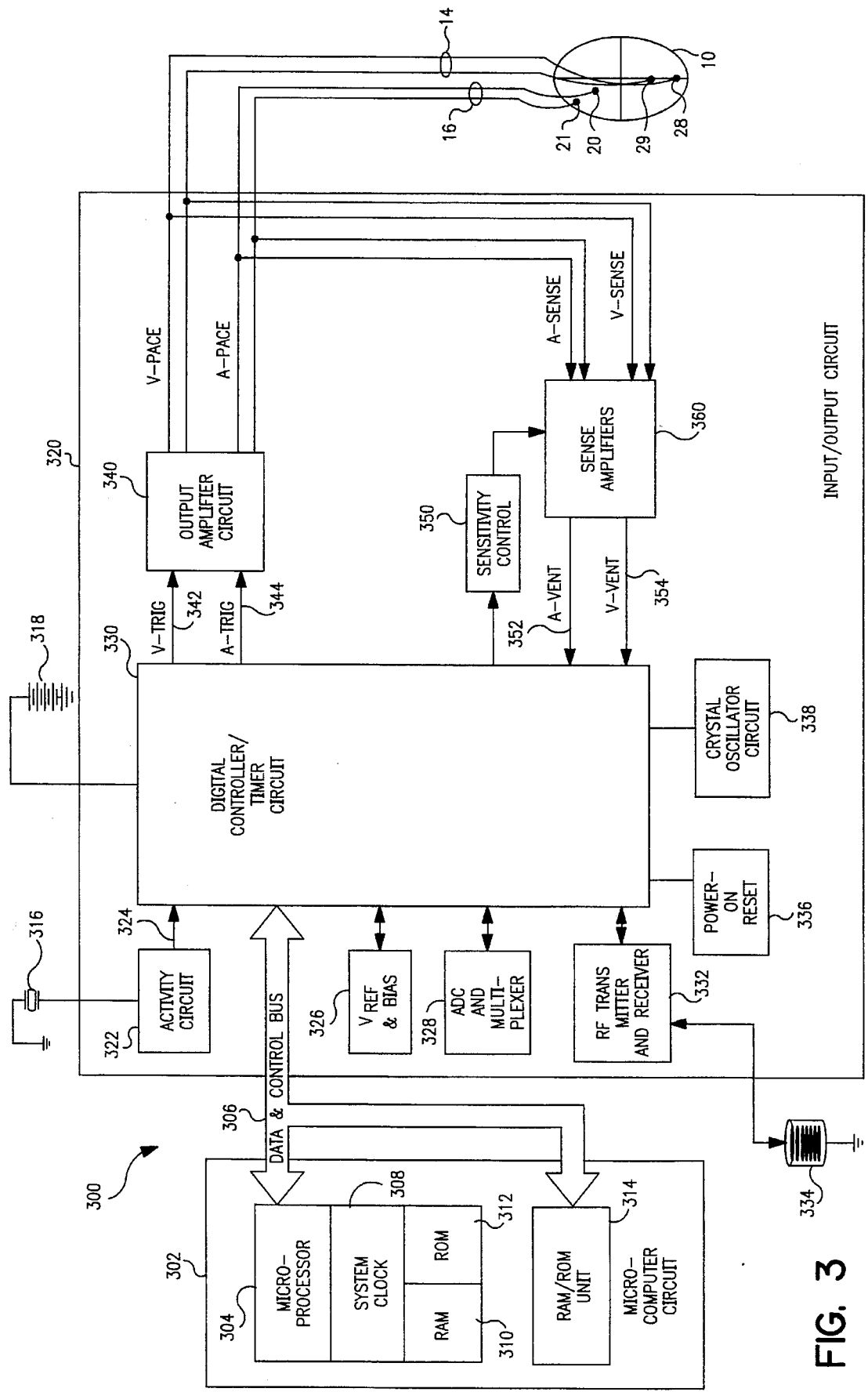
FIG. 3 is a block diagram of the primary functional components of a pacemaker used in the system and method of this invention.

FIG. 3 is a block functional diagram of the pacemaker illustrated in FIG. 1, as connected to a human heart 10. The circuitry illustrated is all located within the conductive housing or can 8 of the pacemaker, as illustrated in FIG. 1, and the bipolar leads 14 and 16 are illustrated schematically as coupled directly to the circuit. However, of course, in the actual device they would be coupled by means of removable electrical connectors inserted in the connector block 12, as illustrated in FIG. 1.

The pacemaker is divided generally into a microcomputer circuit 302 and a pacing circuit 320. A pulse generator circuit 340 includes a ventricular pulse generator circuit coupled to the heart 10 by means of electrodes 29 and 28 on lead 14, as well as an atrial pulse generator circuit coupled to the heart 10 by means of atrial electrodes 20 and 21, located on lead 16. Similarly, pacing circuit 320 includes atrial and ventricular sense amplifiers in sense amplifier circuit 360, coupled to the atrium and ventricle by means of leads 14 and 16 as well. The ventricular sense amplifier provides for separate detection and identification of QRS-wave signals, in a known manner; it may also provide for detection and identification of T-wave signals. The atrial sense amplifier provides for respective identification of P-waves and FFRS signals. The output circuit 340 and sense amplifier circuit 360 may contain pulse generators and sense amplifiers corresponding to any of those presently employed in commercially marketed cardiac pacemakers. Control of timing and other functions within the pacemaker circuit is provided by digital controller/timer circuit 300, which includes a set of timers and associated logic. Digital controller/timer circuit 330 defines the basic pacing interval of the device, which may take the form of an A—A escape interval initiated on atrial sensing or pacing and triggering atrial pacing at the expiration thereof, or may take the form of a V—V escape interval, initiated on ventricular sensing or pacing and triggering ventricular pulse pacing at the expiration thereof. Digital controller/timer circuit 330 similarly defines the A–V escape interval, $AV_{esc}$, discussed in detail below. The specific values of the intervals defined are controlled by the microcomputer circuit 302 by means of data and control bus 306. Sensed atrial depolarizations and FFRSs are communicated to the digital controller/timer circuit 330 on A event line 352; and ventricular depolarizations (QRS-waves) are communicated to the digital controller/timer circuit 330 on V event line 354. In order to trigger generation of a ventricular pacing pulse, digital controller/timer circuit 330 generates a trigger signal on V trig line 342. Similarly, in order to trigger an atrial pacing pulse, digital controller/timer circuit 330 generates a trigger pulse on a trig line 344.

Digital controller/timer circuit 330 also defines time intervals for controlling operation of the sense amplifiers in sense amplifier circuit 360. Typically, digital controller/timer circuit 330 will define an atrial blanking interval following delivery of an atrial pacing pulse, during which atrial sensing is disabled, as well as ventricular blanking intervals following atrial and ventricular pacing pulse delivery, during which ventricular sensing is disabled. Digital controller/timer circuit 330 will also define an atrial refractory period during which atrial sensing is disabled, this refractory period extending from the beginning of the A–V escape interval following either a sensed or paced atrial depolarization, and extending until a predetermined time following sensing of a ventricular depolarization or delivery of a ventricular pacing pulse. Digital controller/timer circuit 330 similarly defines a ventricular refractory period following ventricular sensing or delivery of a ventricular pacing pulse, which is typically shorter than the portion of the atrial refractory period following ventricular sensing or pacing. Digital controller/timer circuit 330 also controls sensitivity settings of the sense amplifiers 360 by means of sensitivity control 350.

In the embodiment illustrated in FIG. 3, the pacemaker is provided with a piezo electric sensor 316 which is intended to monitor patient activity, in order to allow provision of rate responsive pacing, such that the defined pacing rate (A-A escape interval or V—V escape interval) increases with increased demand for oxygenated blood. Sensor 316 generates electrical signals in response to sensed physical activity which are processed by activity circuit 322 and provided to digital controller/timer circuit 330. Activity circuit 332 and associated sensor 316 may correspond to the circuitry disclosed in U.S. Pat. No. 5,052,388, issued to Betzold et at., and U.S. Pat. No. 4,428,378, issued to Anderson et al. incorporated herein by reference in their entireties. Similarly, the present invention may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the present invention may also be practiced in non-rate responsive pacemakers.

Transmission to and from the external programmer 4 illustrated in FIG. 2 is accomplished by means of antenna 334 and associated RF transmitter and receiver 322, which serves both to demodulate received downlink telemetry and to transmit uplink telemetry. Crystal oscillator circuit 338 provides the basic timing clock for the circuit, while battery 318 provides power. Power on reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexor circuit 328 digitizes analog signals and voltage to provide real time telemetry of cardiac signals from sense amplifiers 360, for uplink transmission via RF transmitter and receiver circuit 332. Voltage reference and bias circuit 326, ADC and multiplexor 328, power on reset circuit 336 and crystal oscillator circuit 338 may correspond to any of those presently used in current marketed implantable cardiac pacemakers.

Microcomputer circuit 302 controls the operational functions of digital controller/timer 330, specifying which timing intervals are employed, and controlling the duration of the various timing intervals, via data and control bus 306. Microcomputer circuit 302 contains a microprocessor 304 and associated system clock 308 and on processor RAM circuits 310 and 312, respectively. In addition, microcomputer circuit 302 includes a separate RAM/ROM chip 314. Microprocessor 304 is interrupt driven, operating in a reduced power consumption mode normally, and awakened in response to defined interrupt events, which may include delivery of atrial and ventricular pacing pulses as well as sensed atrial and ventricular depolarizations. In addition, if the device operates as a rate responsive pacemaker, a timed interrupt, e.g., every cycle or every two seconds, may be provided in order to allow the microprocessor to analyze the sensor data and update the basic rate interval (A—A or V—V) of the device. In addition, in a preferred embodiment of the invention, the microprocessor 304 may also serve to define variable A-V escape intervals and atrial and ventricular refractory periods which may also decrease in duration along with decreases in duration of the basic rate interval. Specifically, the microprocessor is used to carry out the routines illustrated in FIGS. 4A, 4B and 6A-6C.

The illustrated circuitry of FIG. 3 is merely exemplary, and corresponds to the general functional organization of most microprocessor controlled cardiac pacemakers presently commercially available. It is believed that the present invention is most readily practiced in the context of such a device, and that the present invention can therefore readily be practiced using the basic hardware of existing microprocessor controlled dual chamber pacemakers, as presently available, with the invention implemented primarily by means of modifications to the software stored in the ROM 312 of the microprocessor circuit 302. However, the present invention many also be usefully practiced by means of a full custom integrated circuit, or any combination of hardware and software.

Figures 4A, 4B:
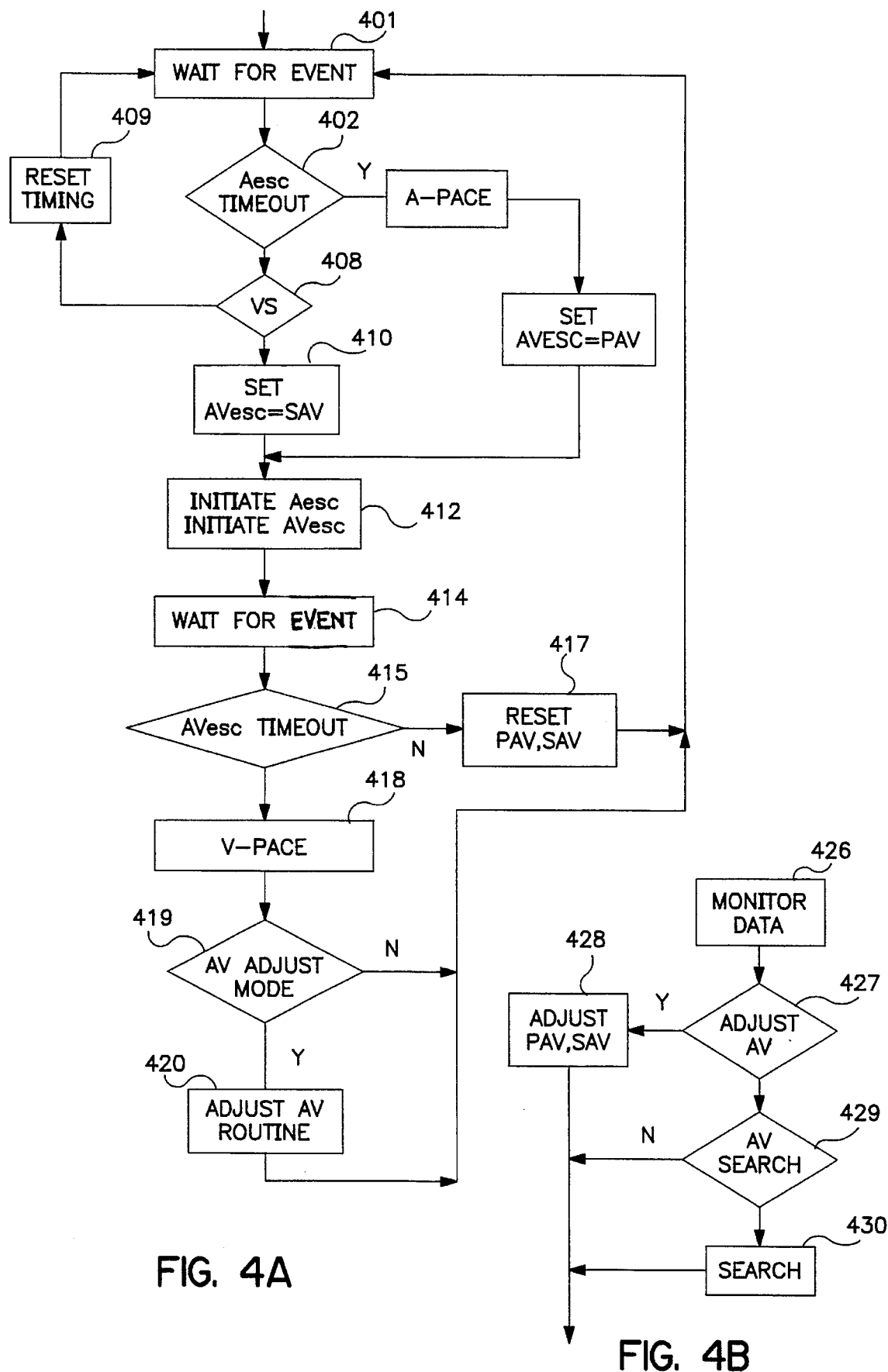
FIG. 4A is a generalized flow diagram illustrating steps taken in synchronous pacing in accordance with this invention, including adjusting AV escape interval for optimizing HOCM therapy.
FIG. 4B is a flow diagram illustrating the primary steps of a pacemaker routine which includes searching to determine a HOCM-optimized AV escape interval.

Referring now to FIG. 4A, there is shown a generalized flow diagram of steps taken by a pacemaker system in accordance with this invention in performing synchronous pacing, with adjustment of $AV_{esc}$ for optimal HOCM therapy. The steps of this flow diagram are suitably carried out by microcomputer circuit 302. This is a simplified flow diagram setting forth only steps pertinent to controlling $AV_{esc}$, and does not include many other steps and responses that occur during each cycle of a typical dual chamber pacemaker. The illustrated logic of FIG. 4A recognizes that the intrinsic AV conduction time following an atrial pace pulse is greater than following a sensed atrial depolarization, by an amount described as "atrial sense offset", or ASO in referenced U.S. application Ser. No. 08/214,933. The $AV_{esc}$ following an atrial pace is defined as PAV; the $AV_{esc}$ following an atrial pace is defined as PAV; the $AV_{esc}$ following an atrial sense is defined as SAV; and PAV=SAV+ASO.

At block 401, the routine of FIG. 4A is waiting for what is expected to be an atrial event. When an event occurs, the routine goes to block 402 and determines whether there has been timeout of the atrial escape interval, $A_{esc}$. If yes, this indicates that an atrial pace (AP) should be delivered, and this is done at block 404. Following this, the routine sets $AV_{esc}$ to PAV, and initiates timeout of $AV_{esc}$. Returning to 402, if there has been no timeout of $A_{esc}$, the pacemaker proceeds to 408, and determines whether there has been an early ventricular sense (VS). If yes, the routine branches to block 409 and resets the timing appropriately, whereafter it returns to block 401. However, as would normally be the case, if at 408 the event is not a VS, meaning that it has been an atrial sense (AS), the routine proceeds to block 410 and sets $AV_{esc}$ to the current value of SAV. Following this, the routine goes to 412 and initiates timeout of the atrial escape interval ($A_{esc}$), and timeout of the AV escape interval, $AV_{esc}$ (either SAV or PAV). Then, at 414, the pacer waits for the next event, normally a ventricular event.

At 415, the pacemaker responds to an event by first determining whether the event was a timeout of $AV_{esc}$. If no, meaning that there was a ventricular sense, the pacemaker proceeds to block 417 and resets PAV and SAV to a shorter value which ensures capture by the next ventricular pace pulse. For example, each of these values can be decremented by 20 or 50 ms, to ensure that succeeding timeouts of $AV_{esc}$ occur early enough for complete capture. It is to be noted, however, that the algorithms discussed below are designed to avoid an occurrence of VS, such that the pacemaker should rarely take this path.

If at 415 there has been a timeout of $V_{esc}$, then the pacemaker proceeds to block 418 and delivers a V pace. Then, at block 419, the pacemaker determines whether it is programmed to go into the AV adjust routine. If no, the routine is done and it exists back to 401. If yes, the pacemaker goes to the adjust AV routine at block 420. Here, the pacemaker analyzes collected data, e.g., VP-FFRS time; FFRS duration; or FFRS or QRS amplitude. With this data in hand, the pacemaker system can adjust the values of PAV and SAV, in accordance with a predetermined algorithm for changing $AV_{esc}$ so as to optimize resultant pre-excitation. Following this, the routine returns to block 401 and waits for the next atrial event.

Note that the pacemaker can be programmed for automatically monitoring AV data and adjusting $AV_{esc}$ each pacemaker cycle, or these steps can be taken on some other periodic or user-programmed basis, within the scope of the invention. For an implanted pacemaker which is set to automatically adjust AV, the pacemaker goes directly to 420. Similarly, for a pacemaker system in accordance with this invention which adapted to be programmed specifically by a physician, the routine exits unless the programming sequence has been activated.

FIG. 4B is a simple flow diagram of the primary steps of an adjust AV routine that includes a "search",or scan, whereby $AV_{esc}$ is varied in accord with a predetermined program. At block 426, the pacemaker system monitors the data from which an indication of AV optimization is derived, e.g. FFRS duration or VP-FFRS time. Following this, at 427, the monitored data is analyzed and a decision is made as to whether the AV delay requires adjustment based upon the monitored data. Specific embodiments of this determination are set forth in FIGS. 6A–6C. The routine then branches to 428 and adjusts the value or values of AV delay. However, if no adjustment is indicated, the routine proceeds to 429 and determines whether AV search is to be undertaken. If no, the routine exists, but if yes the routine goes to block 430 and carries out a search whereby typically the AV escape interval is incremented cyclically or every n cycles toward a value corresponding to the patient's intrinsic conduction. For example, $AV_{esc}$ can be incremented 5 ms every cycle, or every n cycles, until either fusion is detected, or there is a ventricular sense. FIG. 6A gives a specific example of a search.

Figure 5A:
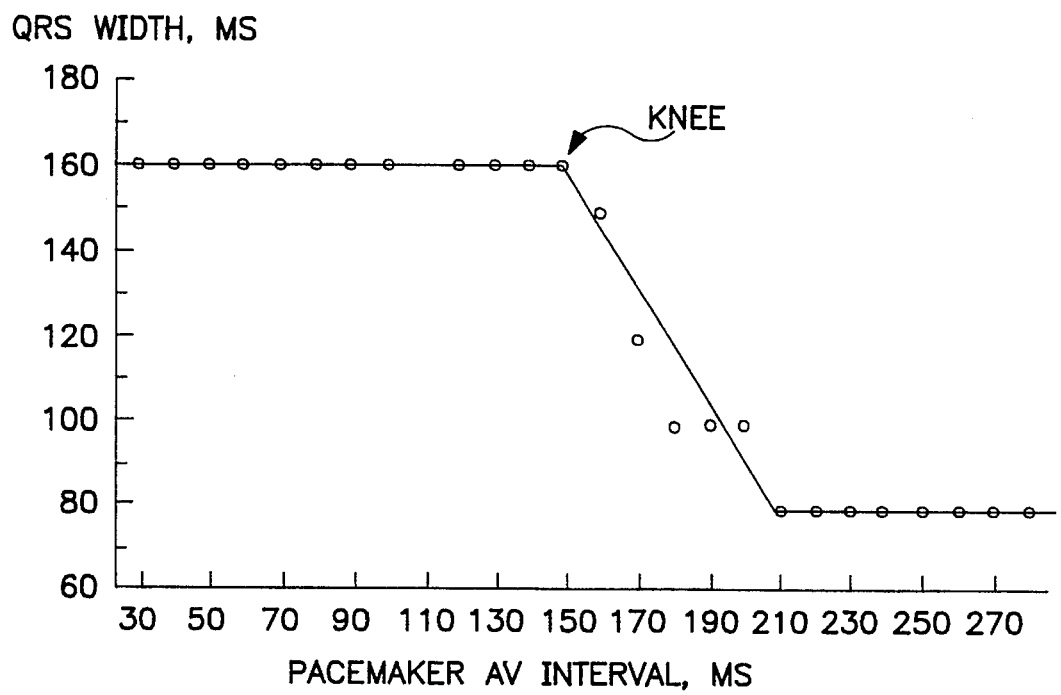
FIG. 5A is a representative data plot of QRS or FFRS duration as a function of pacemaker AV escape interval.

Referring now to FIG. 5A, there is shown a plot of data representative of QRS or FFRS duration (ms) as a function of pacemaker AV escape interval (ms). It is to be noted that a particularly reliable measure of QRS duration can be obtained from the FFRS signal in and around the "fusion" range between full capture by the pacing pulse, and ventricular sense. As is seen in FIG. 5A, the QRS duration is relatively low at higher AV intervals which are greater than the patient's intrinsic PR conduction time, i.e., where a VS occurs before timeout of $AV_{esc}$. However, as $AV_{esc}$ is shortened, it comes into a fusion area where QRS increases up to a knee value (illustrated at about 150 ms); at shorter intervals, where a VP results in full capture, QRS duration is substantially constant. The portion between full capture and failure to capture is termed the fusion area, or range, and the ability to detect duration changes in this area, as seen from FFRS signals, provides the basis for one embodiment of this invention. Although FIG. 5A illustrates QRS data, the FFRS data corresponds directly, and in particular is characterized by the same knee, or breakpoint, between the fusion range and the lower full capture range. The knee is seen to be at the onset of fusion.

Figure 5B:
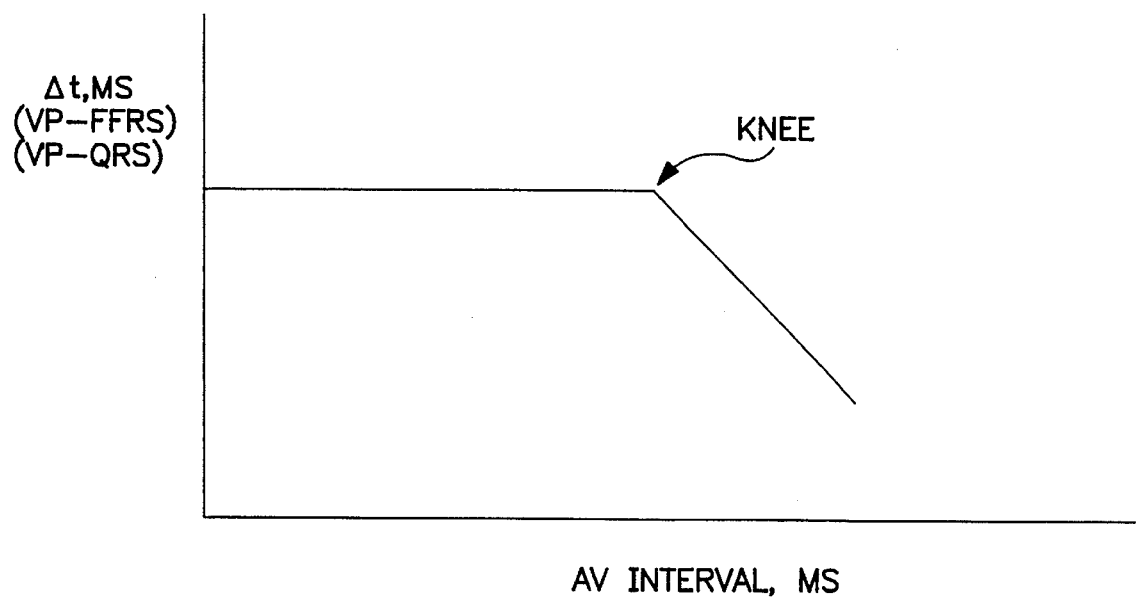
FIG. 5B is a representative plot of VP-FFRS or VP-QRS time interval as a function of pacemaker escape interval.

Referring now to FIG. 5B, there is shown a plot of the time between a delivered ventricular pacing pulse (VP) and the sensed FFRS, i.e., $\Delta t$=VP–FFRS. The VP-FFRS duration is measured from the time of delivery of the ventricular pacing pulse to the time when the leading edge of the FFRS is detected to rise to a predetermined threshold amplitude. The variation of VP-QRS follows the same form, i.e., the duration is longest corresponding to short AV intervals when the delivered pacing pulse captures the heart, and drops during the fusion range. What is important is that the $\Delta t$/AV curve exhibits the same knee characteristic as seen in the QRS/AV curve of FIG. 5A. As used herein, the phrase "VP-FFRS knee" refers to the point on the VP-FFRS vs. AV interval curve where VP-FFRS starts to drop from its maximum value toward lower values at higher AV intervals.

Referring now to FIG. 6A, there is shown a flow diagram of more detailed steps for carrying out a search routine to obtain data from which an adjusted SAV is determined. At 515, the pacemaker system determines whether the ventricular event has been a V sense. If no, meaning that a ventricular pace pulse was delivered, the routine goes to block 535 and determines whether a search flag has been set. If no, meaning that no search is currently in operation, the routine goes to block 536 and determines whether to initiate a search. A search may be triggered either by an external program signal, or by a signal generated automatically by the pacemaker, e.g. after a predetermined number of cycles or a predetermined amount of time. If no search is indicated, the routine exits. However, if a search is indicated, at 529 the pacemaker first decrements the AV delay by a small increment A2, to provide that the search starts at an AV delay which is safely short of the fusion area. Following this, at 537 the search flag is set.

Returning to 535, if it is found that the search flag is set, the routine goes to block 540 takes initial steps for obtaining data. For an embodiment which uses VP-FFRS time, the pacer starts a clock to time out the time from the delivered ventricular pace pulse to the detected FFRS. The pacemaker also generates a sense window connected through control 350 for a predetermined duration adjusted to exclude the T-wave, e.g. up to 300 ms. The sense window acts on the atrial sense amplifier, and the FFRS is channeled through line 352 to circuit 330, where it is detected as shown at flow block 542. Following this, at block 544, the pacemaker system gets and stores the value of the applicable parameter, e.g., VP-FFRS time ($TN_{Nx}$). Thus, the time is obtained from the clock which had been set at 540, and the variable $T_{Nx}$ is stored. In the embodiment where the width of the FFRS signal is utilized, this width is obtained from the FFRS signal and stored. In the embodiment where the amplitude of the FFRS is utilized, the amplitude is obtained and the variable $A_{Nx}$ is stored.

The steps 542, 544 of sensing and processing the FFRS signal are accomplished by standard hardware, preferably also using digital processing techniques. For getting the time of VP-FFRS, a standard edge detector may be utilized in circuit 330 to sense when the leading edge of the FFRS signal has reached a predetermined level, or has increased by a predetermined percentage. For determining width, or duration, the signal is processed to determined when it first rises to a predetermined level, and when it falls back below such level. And amplitude is measured by either a simple peak detector, or other standard amplitude detection circuitry. These standard circuits may be supplemented or replaced by known digital processing techniques, carried out with the aid of microprocessor system 302.

Following the operations at 544, the routine goes to 545 and determines whether the variable X has reached a maximum. This variable corresponds to the number of cycles that data has been taken at the same AV value. If X has not yet reached $X_{max}$, e.g. 5, the routine increments X at 546. If X does equal $X_{max}$, the routine sets X equal to 0 at block 548, and at block 560 increments the value of $AV_N$, setting $AV_N = AV_{N-1} + \Delta 3$, where $\Delta 3$ is a predetermined increment, e.g. 2 or 5 ms. At 561, N is incremented by 1, for purposes of accurate storage at block 544. In this manner, X measurements can be taken at N representative search values of $AV_{esc}$.

Returning to step 515, if a V sense is detected, AV is immediately decremented at 528, e.g., by $\Delta 2 = 20$ ms, to prevent further cycles without pacing capture. At 552, the system determines whether the search flag has been set. If no, this means that there has been a V sense without a search, and the routine exits. If yes, this means that AV has been lengthened to the point where capture is lost. The search flag is reset at 554, and the variable N is set equal to 0 at 555. Then, at 560, the system initiates the Find SAV routine, as described more fully in the embodiments of FIGS. 6B and 6C. Initiation of the Find SAV routine may be done automatically within the pacemaker, or the data can be downloaded to the programmer for analysis and determination of an optimum value of SAV.

Referring now to FIG. 6B, there is shown a first embodiment of the Find SAV routine 560 for obtaining an adjusted SAV as a function of FFRS width (duration). At 601, the average width value ($W_N$) corresponding to the X values of each $AV_N$ during the search is determined. This may be done by any suitable processing technique, preferably obtaining a sample rolling average. Following this step for each value of N, resulting in M values of average width, the variable N is set equal to 1 at 602. At 604 the pacemaker compares the difference of $W_N-W_{N+1}$ against a predetermined increment $\Delta$. This step thus determines whether the QRS width ($W_{N+1}$), as represented by the measured FFRS width, is significantly shorter than the value at the next shorter AV interval ($W_N$). TO allow for jitter and timing vagaries, the algorithm preferably is set to determine a substantial change in width as being only greater than $\Delta$, e.g. 15 ms. If such a differential is not found, the routine goes to 605 and determines whether N has stepped through the maximum number of values for which data is available, i.e., N= M. If no, at 607N is incremented by 1 and the routine returns to step 604. At the point where the differential between adjacent AV values exceeds $\Delta$, the routine branches to block 608 and determines a new SAV to be equal to the just prior value of AV, i.e. SAV (N–1). Following this, the determined value of SAV is displayed at 610. Alternately, for an implanted pacemaker, the new value of SAV can be automatically adopted.

Referring back to the illustrative plot of FIG. 5A, for this data the algorithm of FIG. 6B proceeds to the point where it determines that the AV interval of about 160 ms is the first to have an averaged width which falls outside the allowed range, i.e., the differential of $AV_{N+1}$ to $AV_N$ is greater than $\Delta$. The algorithm then assumes that the AV interval of about 150 ms, AV(N), is an optimum point, and subtracts one AV interval increment to obtain AV (N–1), at approximately 140 ms. By this means, an AV value at or just less than the knee is determined.

Referring now to FIG. 6C, there is shown a flow diagram that corresponds to FIG. 6B, but which determines the optimum value of SAV in terms of $T_N$, the time between the ventricular pace pulse and the evoked response as detected through the FFRS (VP-FFRS). At block 620, the average of $T_N$ is obtained from the X measured values corresponding to each value of N. This produces an array of values of $T_N$ corresponding to the M different values of $AV_N$ utilized during the search routine. Following this, at 622 the variable N is set equal to 1. At 624, $T_N$ is compared to $T_{N+1}$, to see if the difference is greater than a predetermined increment $\Delta$. Note that as AV interval increases, the system is looking for the knee corresponding to a decrease in $T_N$. When this decrease first exceeds the predetermined increment, this indicates the onset of fusion, and the routine branches to block 628 and sets SAV equal to SAV(N–1). The premise in this subroutine is the same as for FIG. 6B, i.e., the first AV interval which corresponds to a substantial decrease in time is just down the slope from the knee. Accordingly, selecting the just prior value of AV, corresponding to $T_{N+1}$, represents a factor of safety. It is seen that if no interval difference as computed at 624 exceeds the predetermined increment, the routine loops continuously until N=M, at which time the information is displayed. The physician can inspect this data and choose from it an optimum value of SAV.

There has thus been disclosed a pacemaker system and method for dual chamber synchronous pacing optimized for cardiomyopathy therapy, and particularly for HOCM therapy. In a preferred embodiment of this invention, the pacemaker system detects the FFRS and processes the signal to determine at least one characteristic thereof. The system collects data representative of a selected FFRS characteristic or several characteristics, over a range of values of AV escape interval, which values include the fusion range or zone. The FFRS characteristic is suitably VP-FFRS time; FFRS duration; or FFRS amplitude; or any combination of these variables. Thus, the parameter for determining AV may be X, where X=fn (amplitude)+fn (duration)+ fn (timing). In another embodiment of the system and method of this invention, the R-wave may be monitored directly and a characteristic derived from it, e.g. amplitude or VP-QRS time, in which case the system utilizes these characteristics in the same manner to determine the optimum adjustment of AV escape interval.

The novel technique of using the FFRS to determine optimal $AV_{esc}$ has been illustrated with the preferred embodiment of scanning, or searching to determine the knee of the VP-FFRS curve, from which a new value of $AV_{esc}$ is determined. However, the pacemaker of this invention further includes monitoring an FFRS characteristic, e.g., VP-FFRS time, or VP-QRS time, to determine when operation may be in the fusion range. Thus, referring back to FIG. 4B, the monitored data can simply be inspected each cycle to see whether there has been a decrease in the interval, i.e., whether a shortening of the VP-FFRS duration indicates the onset of fusion. In this case, even though no search as such has been conducted in order to determine the knee, the pacemaker of this invention senses the onset of fusion and adjusts $AV_{esc}$ by shortening it. The scope of the invention thus embraces ongoing cyclical monitoring of an FFRS characteristic, as well as searching to acquire batch data from which an accurate determination of the knee is obtained.

It is further noted that the system and method as claimed can utilize a number of different configurations. Thus, an implantable pacemaker used in this invention can contain hardware and/or software for control of $AV_{esc}$ upon command from an external programmer; upon command from a "patient activator"; automatically, based on internal logic, e.g., elapsed time or number of pacemaker cycles; or based on some other parameter or criteria being met, e.g., change in one or more sensor levels. Also, the practice of the invention embraces the use of an external pacemaker and the like, and available technology for transmitting data to and from the patient location.

What is claimed is:

1. A dual chamber pacemaker system, having atrial sense means for sensing signals from a patient's atrium, ventricular sense means for sensing ventricular signals from a patient, ventricular pace means for generating and delivering ventricular pacing pulses to said patient's right ventricle, $AV_{esc}$ means for setting and timing an AV escape interval from the occurrence of a sensed atrial signal, sync control means for controlling delivery of ventricular pacing pulses at the time out of said AV escape interval in the absence of a sensed ventricular signal, and FFRS means for detecting FFRSs following delivered ventricular pacing pulses, further comprising FFRS analyzing means for analyzing said detected FFRSs and determining therefrom an indication for adjustment of said AV escape interval, said $AV_{esc}$ means having adjusting means for adjusting said AV escape interval in accordance with said indication.

2. The pacemaker system as described in claim 1, comprising timing means for timing the respective time intervals between delivered ventricular pacing pulses and following detected FFRSs, and wherein said FFRS analyzing means has determining means for determining said indication from said time intervals.

3. The pacemaker system as described in claim 1, wherein said FFRS analyzing means has knee means for determining the $AV_{esc}$ at about which the knee of said time interval occurs.

4. The pacemaker system as described in claim 1, comprising duration means for determining the durations of detected FFRSs, and wherein said FFRS analyzing means has means for determining said indication from said durations.

5. The pacemaker system as described in claim 1, wherein said $AV_{esc}$ means comprises AV search means for periodically increasing said AV escape interval from a value at which a ventricular pace pulse achieves complete capture toward a value at which a ventricular pace pulse fails to achieve complete capture.

6. The pacemaker system as described in claim 5, wherein said FFRS analyzing means has timing means for determining the patient's VP-FFRS knee.

7. The pacemaker system as described in claim 6, wherein said adjusting means comprises means for shortening said AV escape interval to a value less than the AV escape interval corresponding to said knee.

8. The pacemaker system as described in claim 1, comprising search means for varying said AV escape interval through respective values thereof in accord with a predetermined search pattern, and wherein said FFRS analyzing means comprises data means for collecting FFRS data representative of at least one predetermined FFRS characteristic corresponding to each value of AV escape interval within said search.

9. The pacemaker system as described in claim 8, wherein said FFRS analyzing means further comprises fusion means for analyzing said collected data to determine a value of AV escape interval corresponding to the breakpoint between full capture pacing and fusion.

10. The pacemaker system as described in claim 8, comprising programmer means for programming initiation of said search means to carry out said search pattern.

11. The pacemaker system as described in claim 8, comprising external programmer means having said FFRS analyzing means, and telemetry means for telemetering said FFRS data to said external programmer means.

12. The pacemaker system as described in claim 8, wherein said predetermined FFRS characteristic is FFRS duration, and comprising means for comparing the FFRS duration value at a given AV escape interval to the FFRS duration value corresponding to the next shorter value of AV escape interval, and for determining the shortest value of AV escape interval at which said comparison produces a difference greater than a predetermined factor.

13. The pacemaker system as described in claim 1, wherein said analyzing means comprises means for determining the longest AV escape interval corresponding to the occurrence some degree of fusion and for providing an indication of an AV escape interval just shorter than said corresponding interval.

14. The pacemaker system as described in claim 1, further comprising atrial pacing means for delivering atrial pacing pulses, and wherein said $AV_{esc}$ means sets and times an AV escape interval from the occurrence of a delivered atrial pacing pulse.

15. A dual chamber pacemaker system, having atrial sense means for sensing signals from a patient's atrium, atrial pace means for delivering atrial pacing pulses, ventricular sense means for sensing ventricular signals from a patient, ventricular pace means for generating and delivering ventricular pacing pulses to said patient's right ventricle, $AV_{esc}$ means for setting and timing out an AV escape interval from the occurrence of a sensed atrial signal or an atrial pacing pulse, and sync control means for controlling delivery of a ventricular pacing pulse at the time out of a said AV escape interval in the absence of a sensed ventricular signal, comprising AV varying means for varying said AV escape interval in accord with a predetermined search pattern, measure means for detecting a measure of QRS waves evoked by a delivered ventricular pulse at said varied AV escape intervals, programmable batch data means for collecting data representative of respective QRS measure signals and corresponding values of AV escape interval, programmable analyzing means for analyzing said collected data to determine a value of AV escape interval corresponding to the onset of fusion, and said AV escape means having adjusting means for adjusting said AV escape interval as a function of said determined value of AV escape interval corresponding to the onset of fusion.

16. The pacemaker system as described in claim 15, wherein said batch data means comprises means for collecting data representative of the duration of evoked QRS signals at respective escape intervals.

17. The pacemaker system as described in claim 16, comprising FFRS means for detecting FFRS signals from the sensed signals from the patient's atrium, and wherein said analyzing means has means for analyzing said FFRS signals to determine a measure of QRS duration.

18. The pacemaker system as described in claim 15, wherein said batch data means comprises means for collecting data representative of the amplitude of evoked QRS waves.

19. The pacemaker system as described in claim 18, comprising FFRS means for detecting FFRS signals from said sensed signals from the patient's atrium, and wherein said analyzing means comprises means for analyzing said FFRS signals to determine a measure of QRS duration.

20. The pacemaker system as described in claim 15, wherein said batch data means comprises means for collecting data representative of the time intervals between delivered ventricular pace pulses and resulting evoked QRS signals corresponding to a plurality of values of AV escape interval.

21. The pacemaker system as described in claim 20, wherein said batch data means comprises means for detecting FFRS signals, and wherein said analyzing means comprises means for determining time intervals from delivered ventricular pacing pulses to said FFRS signals.

22. The pacemaker system as described in claim 15, wherein said system further comprises an external programmer means for activating said batch data means and said analyzing means.

23. The pacemaker system as described in claim 22, further comprising external ECG leads for providing the signals to said atrial sense means and said ventricular sense means.

24. The pacemaker system as described in claim 22, further providing telemetry means for transferring said collected data to said programmer.

25. A dual chamber pacemaker system, having atrial sense means for sensing signals from a patient's atrium, ventricular sense means for sensing ventricular signals from a patient, ventricular pace means for generating and delivering ventricular pacing pulses to said patient's right ventricle, $AV_{esc}$ means for setting and timing out an AV escape interval from the occurrence of a sensed atrial signal, and sync control means for controlling delivery of a ventricular pacing pulse at the time out of a said AV escape interval in the absence of a sensed ventricular signal, comprising scan means for controlling said $AV_{esc}$ means to vary said AV escape interval through successive values thereof, timing means for determining, corresponding to each scanned value of AV escape interval, a measure of the time duration between a delivered ventricular pacing pulse and a following evoked QRS, analyzing means for analyzing the said time duration measures to determine a value of AV escape interval corresponding optimal pre-excitation, and adjust means for adjusting the value of said AV escape interval in response to a determination of optimal pre-excitation.

26. The pacemaker system as described in claim 25, wherein said analyzing means determines a value of AV escape interval corresponding to the onset of fusion.

27. The pacemaker system as described in claim 26, wherein said timing means is operative continuously each pacemaker cycle having a delivered ventricular pacing pulse, and said adjust means adjusts the value of AV escape interval upon a determination of onset of fusion.

28. The pacemaker system as described in claim 25, comprising programmer means for enabling said timing means and said analyzing means.

29. The pacemaker system as described in claim 28, comprising ECG leads connected from said patient to said atrial sense means and said ventricular sense means.

30. The pacemaker system as described in claim 28, comprising telemetry means for transmitting data representative of said measures of time duration to said programmer.

31. A method of dual chamber synchronous pacing of a patient to provide CHF therapy, comprising detecting FFRS signals from said patient, processing said FFRS signals to obtain from them a predetermined characteristic thereof, analyzing said obtained characteristics to determine therefrom an indication of adjustment of the pacemaker AV escape interval and adjusting same in accordance with said indication, and then delivering ventricular pacing pulses to said patient at said adjusted AV escape interval following atrial events.

32. The method of claim 31, comprising determining an optimal AV escape interval from said FFRS characteristic, and delivering ventricular pacing pulses at said optimal AV escape interval.

33. The method of claim 32, comprising determining measures of FFRS duration corresponding to respective values of AV escape interval, and selecting said optimal value of AV escape interval at or just short of the knee of said FFRS duration.

34. The method of claim 32, comprising determining VP-FFRS times corresponding to respective values of AV escape interval, and selecting said optimal value of AV escape interval at or just short of the knee of said times.

* * * * *